United States Patent [19]

Krimm et al.

[11] 3,966,785

[45] June 29, 1976

[54] PROCESS FOR THE PREPARATION OF BISPHENOL BISCHLOROCARBONIC ACID ESTERS

[75] Inventors: Heinrich Krimm, Krefeld; Hermann Schnell, Krefeld-Uerdingen; Hans-Helmut Schwarz, Krefeld, all of Germany

[73] Assignee: Bayer Aktiengesellschaft, Germany

[22] Filed: Mar. 4, 1975

[21] Appl. No.: 555,148

[30] Foreign Application Priority Data
Mar. 6, 1974 Germany.......................... 2410668

[52] U.S. Cl. ............................................. 260/463
[51] Int. Cl.² ...................................... C07C 68/00
[58] Field of Search .................................. 260/463

[56] References Cited
UNITED STATES PATENTS

| | | | |
|---|---|---|---|
| 3,170,946 | 2/1965 | Kilsheimer et al.................. | 260/463 |
| 3,189,640 | 6/1965 | Dietrich et al...................... | 260/463 |
| 3,211,775 | 10/1965 | Stephens et al..................... | 260/463 |
| 3,275,674 | 9/1966 | Bottenbruch et al............... | 260/463 |
| 3,312,661 | 4/1967 | Kurkjy et al...................... | 260/463 X |
| 3,312,662 | 4/1967 | Kurkjy et al...................... | 260/463 X |

FOREIGN PATENTS OR APPLICATIONS
878,115  9/1961  United Kingdom................. 260/463

*Primary Examiner*—Joseph Paul Brust
*Attorney, Agent, or Firm*—Connolly and Hutz

[57] ABSTRACT

A continuous process for the preparation of a bisphenol bischlorocarbonic acid ester, wherein a hydroquinone or a bisphenol dissolved in excess alkali metal hydroxide solution is reacted with 2.5 to 5.0 mol of phosgene (per mol of the dihydroxy compound) which is dissolved in a suitable solvent for the bischlorocarbonic acid ester formed in the reaction at a pH value of at least 12 and a temperature of 0° to 50°C under vigorous mixing of the reactants and unidirectional flow conditions and the organic layer thus obtained is separated wherefrom the bisphenol bischlorocarbonic acid ester is isolated by distillation and/or crystallization.

9 Claims, No Drawings

PROCESS FOR THE PREPARATION OF BISPHENOL BISCHLOROCARBONIC ACID ESTERS

This invention relates to a continuous process for the preparation of bischlorocarbonic acid esters of aromatic dihydroxy compounds by a phase interface process.

Usually bisphenol bischlorocarbonic acid esters are prepared by reacting an aromatic dihydroxy compound with excess phosgene in the presence of a tertiary amine. This process is dangerous because the total quantity of phosgene required must be placed in the reaction vessel which, in many cases, forms together with the tertiary amine resinous complexes which are only slightly soluble at low temperatures and start to react only at higher temperatures, when the reaction may be vigorous and uncontrollable. Moreover processing of the reaction product is difficult and expensive, since the tertiary amines must be separated in the form of the aqueous solutions of their hydrochlorides and regenerated with alkali.

An alternative method comprises reacting a bisphenol with excess phosgene in the presence of a nitrogen compound such as an acid amide, nitrile or quaternary ammonium salt as catalyst. Here again, the total quantity of phosgene must be placed into the reaction vessel and the reaction temperature must be high enough for the phosgene to boil to obtain a sufficiently high reaction velocity.

Since hydrogen chloride is split off at the same time, recycling of the phosgene from the gaseous phase by an efficient cooling system is difficult. Moreover, the process entails difficult problems of corrosion.

These dangers and difficulties are obviated by the present invention which provides a continuous process for the preparation of a bisphenol bischlorocarbonic acid ester, wherein a hydroquinone or an aromatic dihydroxy compound of the general formula I

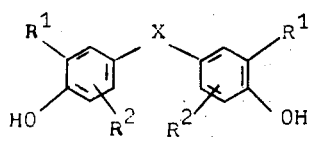

I in which X represents an alkylene or alkylidene, preferably with 1 to 6 carbon atoms, cycloalkylene or cycloalkylidene with preferably 5 to 15 carbon atoms, O, S, $SO_2$ or

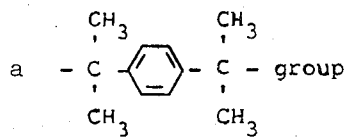

and $R^1$ and $R^2$ which may be the same or different, represent an alkyl group with 1 to 4 carbon atoms, chlorine or bromine atom dissolved in excess alkali metal hydroxide solution is reacted with 2.5 to 5.0 mol of phosgene (per mol of the dihydroxy compound) which is dissolved in a suitable solvent for the bischlorocarbonic acid ester formed in the reaction at a pH value of at least 12 and a temperature of 0 – 50°C under vigorous mixing of the reactants and unidirectional flow conditions and the organic layer thus obtained is separated wherefrom the bisphenol bischlorocarbonic acid ester is isolated by distillation and/or crystallisation.

The quantity of 1 to 30% aqueous alkali metal hydroxide solution (sodium or potassium hydroxide solution) is calculated to maintain the pH above 12 during the whole reaction, i.e. from about 4 to 14 mol of alkali metal solution per mol of bisphenol.

Bisphenols suitable for the process according to the invention include, for example, dihydroxy diarylalkanes such as 2,2-bis-(4-hydroxyphenyl)-propane (bisphenol A); 2,2-bis-(3,5-dichloro-4-hydroxyphenyl)-propane (tetrachlorobisphenol A); 2,2-bis-(3,5-dibromo-4-hydroxyphenyl)-propane (tetrabromobisphenol A); 2,2-bis-(3,5-dimethyl-4-hydroxyphenyl)-propane (tetramethyl bisphenol A); 1,1-bis-(4-hydroxyphenyl)-diisopropyl benzene (trinuclear bisphenol); hydroquinone; bis-(4-hydroxyphenyl)-sulphide; bis-(4-hydroxyphenyl)-sulphone or bis-(4-hydroxyphenyl) ether. The substances mentioned here are only a selection and do not restrict the choice of bisphenols suitable for the process.

Suitable solvents for the bischlorocarbonic acid esters and thus for the phosgene include aromatic hydrocarbons such as benzene, toluene and xylene, chlorinated hydrocarbons such as methylene chloride, ethylene chloride, dichloropropane, chloroform, carbon tetrachloride, 1,2-dichloroethane, chlorobenzene and the chlorotoluenes.

In addition, any solvents which are immiscible with water and capable of dissolving the bischlorocarbonic acid esters formed may in principle be used.

The quantity of phosgene required for preparing the bischlorocarbonic acid esters is preferably 2.5 to 5.0 mol per mol of dihydroxy compound, 3.5 to 4.0 mol of phosgene per mol of dihydroxy compound being more preferably used. If these proportions are used and the pH is kept above 12.0, yields between 80 and 95 % of the theoretical yield, based on the quantity of dihydroxy compounds used, may be obtained. The conversion of dihydroxy compounds is almost quantitative.

The reaction according to the invention is carried out in reaction tubes long enough to ensure complete reaction of the bisphenol at the given rate of throughput and reaction temperature. The diphasic reaction material is mixed by a stirrer extending through the whole length of the reaction tube, e.g. a shelved stirrer, or by a uniform stream of inert gas (bubble column). The phosgene solution and the solution of dihydroxy compound in excess alkali metal hydroxide solution are fed simultaneously into the reaction tube and at the same height. The reaction temperatures are generally from 0° to 50°C, preferably from 0° to 25°C.

The bischlorocarbonic acid ester obtained is isolated from the reaction mixture after removal of the aqueous reaction phase, which can be achieved within a very short time (less than 5 minutes) by known methods using known apparatus such as separating vessels or centrifuges. Isolation of the bischlorocarbonic acid ester can be achieved e.g. by crystallisation by cooling, if indicated after removal of part of the solvent by distillation, or it can be obtained by evaporation of the solvent followed by distillation of the residue.

Very pure bischlorocarbonic acid esters can be obtained if, before the bischlorocarbonic acid ester is isolated, the organic reaction phase is washed free from electrolytes with water. This again is suitably carried out with known systems such as mixers/separators or washing centrifuges.

Bisphenol bischlorocarbonic acid esters are valuable intermediate products for polycondensation reactions, e.g. for the production of polycarbonates and polyurethanes.

EXAMPLE 1 a. Bisphenol A-bischlorocarbonic acid ester

A solution of 912 g (4 mol) of bisphenol A in 12 l of 2n sodium hydroxide solution is fed into the upper end of a vertical reaction tube 50 mm in diameter and 500 mm in length. The tube has a cooling jacket supplied with icewater and inside the tube is a 6-bladed shelved stirrer (length of blades 40 mm, width 20 mm) rotating at 380 revs. per minute. The solution is pumped through the reactor at a rate of 2136 ml per hour while 1240 g of phosgene (12.4 mol) dissolved in 12 l of methylene chloride are pumped in at the same time and at the same level into the tube. The reaction temperature inside the tube is 5° to 8°C. The reaction material is separated portionwise in the separating funnel and the organic layer is dried over sodium sulphate and distilled. 1300 g of colourless bisphenol bischlorocarbonic acid ester distil over at 170° to 175°C and 0.1 Torr and immediately crystallise in the receiver.

The yield was 92% of the theory, with a melting point of 91° to 92°C.

The saponifiable chlorine content was 20.0 to 20.% (calculated 20.1%).

b. Polyurethane

A solution of 35.3 g (0.1 mol) of the bischlorocarbonic acid ester of 2,2-bis-(p-hydroxyphenyl)-propane obtained according to a) in 200 ml of methylene chloride is added dropwise with vigorous stirring over a period of about 1 hour at 15° to 35°C to a mixture of a solution of 25.4 g (0.1 mol) of 2,2-bis-(p-methylaminophenyl)-propane in 300 ml of methylene chloride and a solution of 8.8 g (0.22 mol) of sodium hydroxide in 80 ml of water after the addition of 0.2 ml of triethylamine as catalyst. The reaction mixture is then left to react for two to three hours at the same temperature until the organic solution of the resulting polyurethane has the desired viscosity. A clear, colourless product with a relative viscosity (in methylene chloride solution) of 1.6 is obtained. It can be processed into shaped articles such as fibres, films or foils both from solution and from the melt. The freezing temperature determined by the DTA-method is 155°C. The decomposition temperature is above 360°C.

EXAMPLE 2

986 g (4 mol) of 2,2-bis-(4-hydroxyphenyl)-butane dissolved in 10 l of 10% sodium hydroxide solution are reacted with 1200 g of phosgene dissolved in 12 l of methylene chloride solution in the apparatus described in Example 1. The reaction is carried out as described in Example 1. The yield of the corresponding bischlorocarbonic acid ester is 88% of the theory.

EXAMPLE 3

872 g (4 mol) of di-(4-hydroxyphenyl)-sulphide dissolved in 12 l of 10% sodium hydroxide solution are reacted with 1250 g of phosgene dissolved in 11 l of chlorobenzene in the apparatus described in Example 1. The reaction is carried out as described in Example 1.

We claim:

1. A continuous process for the preparation of a bisphenol bischlorocarbonic acid ester which comprises reacting a hydroxy compound which is a hydroquinone or an aromatic dihydroxy compound of the formula

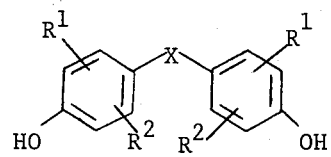

wherein X is alkylene, alkylidene, cycloalkylene, cycloalkylidene, O, S, SO$_2$ or

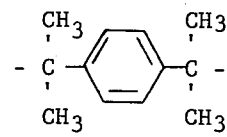

and R$^1$ and R$^2$, which may be the same or different, are each alkyl, chlorine or bromine, said hydroxy compound being dissolved in excess alkali metal hydroxide solution as the sole acid binding agent, with from 2.5 to 5.0 mol, per mol hydroxy compound, of phosgene which is dissolved in a solvent for the bischlorocarbonic acid ester formed in the reaction, at a pH of above 12 and at a temperature of from 0° to 50°C. under vigorous mixing of the reactants and uni-directional flow conditions, separating the organic layer thus obtained and isolating the bisphenol bischlorocarbonic acid ester therefrom by distillation, crystallization or a combination thereof.

2. The process as claimed in claim 1 wherein X is an alkylene or alkylidene having 1 to 6 carbon atoms or cycloalkylene or cycloalkylidene having 5 to 15 carbon atoms.

3. The process as claimed in claim 1 wherein at least one of R$^1$ and R$^2$ is alkyl having 1 to 4 carbon atoms.

4. The process as claimed in claim 1, wherein from 3.5 to 4.0 mol of phosgene are reacted with 1 mol of dihydroxy compound.

5. The process as claimed in claim 1, wherein the hydroquinone or the dihydroxy compound is dissolved in from 4 to 14 mol of a 1 to 30% aqueous alkali metal hydroxide solution.

6. The process as claimed in claim 1, wherein the dihydroxy compound is 2,2-bis-(4-hydroxyphenyl)-propane; 2,2-bis-(3,5-dichloro-4-hydroxyphenyl)-propane; 2,2-bis(3,5-dibromo-4-hydroxyphenyl)-propane; 2,2-bis-(3,5-dimethyl-4-hydroxyphenyl)-propane; 1,1-bis-(4-hydroxyphenyl)-diisopropyl benzene; hydroquinone; bis-(4-hydroxyphenyl)-sulphide; bis-(4-hydroxyphenyl)-sulphone or bis-(4-hydroxyphenyl)-ether.

7. The process as claimed in claim 1, wherein the phosgene is dissolved in an aromatic hydrocarbon or chlorinated hydrocarbon.

8. The process as claimed in claim 7, wherein the solvent is benzene, toluene, xylene, methylene chloride, ethylene chloride, dichloropropane, chloroform, carbon tetrachloride, 1,2-dichloroethane, chlorobenzene or chlorotoluane.

9. The process according to claim 1, wherein the reaction is carried out in a reaction tube which is continuously charged with the solution of said dihydroxy compound and the phosgene solution at the same time and at the same height.

* * * * *